US006383220B1

(12) United States Patent
van Blitterswijk et al.

(10) Patent No.: US 6,383,220 B1
(45) Date of Patent: May 7, 2002

(54) ARTIFICIAL SKIN

(75) Inventors: C. A. van Blitterswijk, Hekendorp; Annette G. M. van Dorp, Rijin; M. Ponec, Leiderdorp; J. U. Riesle, Amsterdam, all of (NL)

(73) Assignee: IsoTis N.V., Bilthoven (NL)

( * ) Notice: Subject to any disclaimer, the term of this patent is extended or adjusted under 35 U.S.C. 154(b) by 0 days.

(21) Appl. No.: 09/451,520

(22) Filed: Nov. 30, 1999

(30) Foreign Application Priority Data

Nov. 30, 1998 (EP) ............................................. 98204031
Dec. 11, 1998 (EP) ............................................. 98204203

(51) Int. Cl.⁷ ................................................. A61F 2/10
(52) U.S. Cl. ................................. 623/15.12; 623/15.11
(58) Field of Search ............................. 623/15.11, 15.12

(56) References Cited

U.S. PATENT DOCUMENTS

| 3,908,201 A | | 9/1975 | Jones et al. .......................... 3/1 |
| 4,947,840 A | * | 8/1990 | Yannas et al. ............... 128/156 |
| 4,985,036 A | * | 1/1991 | Lommen et al. ............... 623/15 |
| 5,147,401 A | | 9/1992 | Bakker et al. ................. 623/15 |
| 5,376,118 A | * | 12/1994 | Kaplan et al. ................. 623/11 |
| 5,480,436 A | * | 1/1996 | Bakker et al. ................. 623/11 |

FOREIGN PATENT DOCUMENTS

| EP | 0 243 132 | 10/1987 |
| EP | 0 357 155 | 3/1990 |
| EP | 0 416 702 | 3/1991 |
| WO | WO 93/21858 | 11/1993 |

OTHER PUBLICATIONS

Morgan and Yarmush, "Bioengineered Skin Substitutes," *Science & Medicine*, pp. 6–15 (Jul./Aug. 1997).
Wood and Harris, "Reconstructed human skin: transplant, graft or biological dressing?" Chap. 4, pp. 65–85, *Essays in Biochemistry*, eds. Apps and Tipton, Portland Press (1995).
Yannas, "Artificial Skin Dermal Equivalents," *Biomed. Eng. Handbook*, pp. 2025–2038 (1995).

* cited by examiner

*Primary Examiner*—Corrine McDermott
*Assistant Examiner*—Thomas Barrett
(74) *Attorney, Agent, or Firm*—Banner & Witcoff, Ltd.

(57) ABSTRACT

The invention relates to an artificial skin based on a copolymer of a polyalkylene glycol and an aromatic polyester, which skin has a thickness between 50 and 2000 μm, and which skin has an upper and a lower side, both having a macroporosity between 10% and 95%.

72 Claims, No Drawings

ARTIFICIAL SKIN

Priority is hereby claimed to EP 98204031.3 filed Nov. 30, 1998 and EP 98204203.8 filed Dec. 11, 1998.

The invention relates to artificial skin which is suitable for wound covering, and which can be used externally on various types of wounds.

Human skin forms a barrier against adverse external influences such as infections. If part of the skin is damaged, as for example in the case of a burn, complications usually arise. These complications are due to the protective function of the skin being lost, as a result of which microbial invasion may occur, and to a substantial loss of moisture that may take place at the place of the wound.

Many studies have been carried out in order to provide an artificial skin which is able to take over all, or a large part of the functions of natural skin during the period that the wound is not covered by an epidermis and dermis. To this end, the artificial skin preferably comprises autologous cells provided on a scaffold. Alternatively, the artificial skin itself may serve as carrier material for cultured autologous keratinocytes and/or fibroblasts, which have a favorable influence on the recovery of the epidermis and/or dermis. Either way, it is desired that an artificial skin, or that a scaffold material comprised by the artificial skin, has suitable properties to serve as carrier for said cells.

An artificial skin of this type must, however, satisfy various requirements. On the one hand, it should provide a barrier, so that the wound is closed to bacteria and the like, and so that substantial moisture loss is avoided. On the other hand, it must be possible for adequate water vapor transport to take place through the artificial skin. During this transport, nutrients from the underlying tissue may reach the recovering skin in sufficient quantity. Another important requirement is that the artificial skin adheres to the underlying wound bed immediately after its application to the wound. Furthermore, a permanent adhesion must be formed as a result of ingrowth of tissue.

In U.S. Pat. No. 5,147,401, an artificial skin is disclosed, of which the outer surface (the surface facing away from a wound to which the skin is to be applied) is virtually closed. This is achieved, in one embodiment, by providing a bi-layer system comprising an upper layer, which is dense and non-porous, on top of a lower layer, which is porous. In a different embodiment, this is achieved by providing a single-layer system of a segmented material, so that one of the sides of the skin is virtually closed, and the other side is fairly open.

It has now been found that when the outer surface of the artificial skin is virtually closed, a poor adherence of the skin to a wound may be observed. Under certain conditions, the artificial skin shows more or less a 'curling-up effect', in that the edges of the skin are forced away from the wound, leading to a poor adherence.

Of course, when the adherence of the artificial skin to the wound is unsatisfactory, the protection of the wound by the artificial skin is equally unsatisfactory. It is therefore an object of the present invention to provide an artificial skin which shows an improved adherence.

Surprisingly, the desired improved adherence may be obtained by the provision of an artificial skin comprising an upper and a lower side, both of which are porous. Thus, the invention relates to an artificial skin based on a copolymer of a polyalkylene glycol and an aromatic polyester, which skin has a thickness between 50 and 2000 $\mu$m, and which skin has an upper and a lower side, both having a macroporosity between 10% and 95%.

An artificial skin according to the invention adheres very well to a wound when applied thereto. Under many circumstances, adherence is achieved in a period of a few minutes after application. The so-called 'curling-up effect' that has been observed with the prior art artificial skins has not been found to occur with the present skin. Furthermore, the artificial skin of the invention provides a highly suitable carrier for autologous cells, thus enabling tissue repair.

An artificial skin according to the invention is based on a specific copolymer, which is biodegradable. Advantageously, the biodegradability (the rate of degradation under certain conditions) may be controlled, depending on the envisaged site of application of the artificial skin.

The specific copolymer on which the present skin is based, is a copolymer of a polyalkylene glycol and an aromatic polyester. In a preferred embodiment, an artificial skin according to the invention is a single-layer system composed of the specific copolymer.

Preferably, the copolymer comprises 40–80 wt. %, more preferably 50–70 wt. % of the polyalkylene glycol, and 60–20 wt. %, more preferably 50–30 wt. % of the aromatic polyester. A preferred type of copolymers according to the invention is formed by the group of block copolymers.

Preferably, the polyalkylene glycol has a weight average molecular weight of from 150 to 4000, more preferably of 200 to 1500. The aromatic polyester preferably has a weight average molecular weight of from 200 to 5000, more preferably of from 250 to 4000. The weight average molecular weight of the copolymer preferably lies between 20,000 and 200,000, more preferably between 50,000 and 120,000. The weight average molecular weight may suitably be determined by gel permeation chromatography (GPC). This technique, which is known per se, may for instance be performed using tetrahydrofuran as a solvent and polystyrene as external standard.

In a preferred embodiment, the polyalkylene glycol component has units of the formula —OLO—CO—Q—CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycols are chosen from the group of polyethylene glycol, polypropylene glycol, and polybutylene glycol and copolymers thereof, such as poloxamers. A highly preferred polyalkylene glycol is polyethylene glycol.

The terms alkylene and polyalkylene generally refer to any isomeric structure, i.e. propylene comprises both 1,2-propylene and 1,3-propylene, butylene comprises 1,2-butylene, 1,3-butylene, 2,3-butylene, 1,2-isobutylene, 1,3-isobutylene and 1,4-isobutylene (tetramethylene) and similarly for higher alkylene homologues. The polyalkylene glycol component is preferably terminated with a dicarboxylic acid residue —CO—Q—CO—, if necessary to provide a coupling to the polyester component. Group Q may be an aromatic group having the same definition as R, or may be an aliphatic group such as ethylene, propylene, butylene and the like.

The polyester component preferably has units —O—E—O—CO—R—CO—, wherein O represents oxygen, C represents carbon, E is a substituted or unsubstituted alkylene or oxydialkylene radical having from 2 to 8 carbon atoms, and R is a substituted or unsubstituted divalent aromatic radical.

In a preferred embodiment, the polyester is chosen from the group of polyethylene terephthalate, polypropylene terephthalate, and polybutylene terephthalate. A highly preferred polyester is polybutylene terephthalate.

The preparation of the copolymer will now be explained by way of example a polyethylene glycol/polybutylene terephthalate copolymer. Based on this description, the skilled person will be able to prepare any desired copolymer within the above described class. An alternative manner for preparing polyalkylene glycou/polyester copolymers is disclosed in U.S. Pat. No. 3,908,201.

A polyethylene glycol/polybutylene terephthalate copolymer may be synthesized from a mixture of dimethyl terephthalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene. In this step the polyethyene glycol substantially does not react. After transesterification, the temperature is raised slowly to about 245° C., and a vacuum (finally less than 0.1 mbar) is achieved. The excess butanediol is distilled and a prepolymer of butanediol terephthalate condenses with the polyethylene glycol to form a polyethylene/polybutylene terephthalate copolymer. A terephthalate moiety connects the polyethylene glycol units to the polybutylene terephthalate units of the copolymer and thus such copolymer also is sometimes referred to as a polyethylene glycol terephthalate/polybutylene terephthalate copolymer (PEGT/PBT copolymer).

The thickness of an artificial skin according to the invention will depend on the envisaged site of application of the skin. Generally, the thickness will be within a range of 50–2000 $\mu$m. The skilled person will be able to select a suitable thickness, given a certain site of application of the skin.

An important aspect of an artificial skin according to the invention is that it has a macroporosity between 10 and 95%, on both sides of the skin. In other words, both the side of the skin facing the wound to which the skin is to be applied, and the side of the skin facing away from the wound have said macroporosity. Preferably, the macroporosity is at least 15%, more preferably at least 20%. It has been found that a skin having this specific macroporosity adheres very well to a wound.

The size of the pores in an artificial skin according to the invention preferably lies between 20 and 500 $\mu$m, more preferably between 50 and 250 $\mu$m.

In a preferred embodiment, particularly when before or after implantation of the artificial skin keratinocytes are applied on top of the skin, the pore size varies within the skin. Preferably, the pores at the upper side of the skin, which faces away from a wound to which the skin is to be applied, are smaller than the pores at the lower side of the skin. According to this embodiment, the chance of microorganisms finding their way through the skin into a wound, and of moisture finding its way through the skin out of the wound are very small. Moreover, the ingrowth of keratinocytes into the artificial skin is substantially prevented, while a suitable porosity of the artificial skin is still present, providing a favorable diffusion profile for nutrients and waste products.

Preferably, in accordance with this embodiment, the diameter of the pores at the upper side of the skin lies between 0.2 and 40 $\mu$m, preferably between 0.4 and 2 $\mu$m. The porosity at the upper side of the skin preferably is higher than 15%. The diameter of the pores at the lower side of the skin preferably lies between 20 and 300 $\mu$m, more preferably between 50 and 250 $\mu$m.

An important advantage of an artificial skin according to the invention is that it forms a highly suitable substrate for culturing epithelial cells,.such as keratinocytes. It has also been found to be feasible to culture fibroblasts on or within the artificial skin. Due to the porous character of the present skin, the fibroblasts can grow both on the upper and on the lower side of the skin, as well as within the skin. The keratinocytes will normally be provided on top of the skin.

If necessary, a possible delay in the initial cell growth on the present skin may be overcome by improving the cell adhesion using, for instance, laminin, collagen (type IV), proteoglycans or fibronectin, which may be applied by (pre)coating to the surface of the material which is to be covered. Improvement of the initial cell growth may further be attained by modification of the surface of the artificial skin. This modification can, inter alia, be carried out by a plasma or glow discharge treatment, radiation, monomer grafting or hydrolytic etching (e.g. with sulfuric acid).

Accordingly, the invention also relates to the therapeutic use of an artificial skin as described herein above. An important example of said use concerns the use of the skin as wound-covering material, particularly in the case of deep or large wounds, such as burns.

When the artificial skin is used per se, that is without providing it with cells prior to implantation in a patient, it may be advantageous to cover the wound to which the artificial skin has been applied with a semi-permeable membrane. This membrane ensures a suitable barrier against microbial invasion and loss of moisture until cells of the patient surrounding the wound have taken over the barrier function of said membrane, or until the membrane may be replaced by an epidermal graft or a cultivated cornified keratinocyte sheet, at which time the membrane may be removed. For a general discussion of how artificial skin may be applied to a patient, reference is made to Morgan et al., Science & Medicine, July/August 1997, pp. 6–15, Yannas, Biomedical Engineering Handbook, CRC Press, 1995, pp. 2025–2038, and Wood et al., in Essays in Biochemistry, Ed. Apps and Tipton, Portland Press, Vol. 29, 1995, pp. 65–85.

Preferably, the artificial skin is provided with autologous epithelial cells and/or fibroblasts when it is applied to a wound. These cells may be obtained from a biopsy taken from the human or animal to be treated. According to the invention, it is possible to culture these autologous cells on the artificial skin both in-vitro and in-vivo. In case the artificial skin is provided with a stratified corneum prior to implantation, the use of a semi-permeable membrane will generally not be necessary.

In case the cells are cultured on the skin in-vitro, it has been found highly advantageous when the artificial skin comprises a calcium phosphate coating. This coating facilitates the adhesion of the cells to the artificial skin. The calcium phosphate may be applied to the artificial skin by soaking the skin into a highly concentrated calcifying solution at low temperature. The calcifying solution is preferably composed of at least calcium and phosphate ions, and optionally of-magnesium, carbonate, sodium and chloride ions, which are dissolved into water by bubbling carbon dioxide gas. During the natural release of carbon dioxide gas or its exchange with air, the pH of the calcifying solution is increased and the saturation is raised until the nucleation of carbonated calcium phosphate crystals on the surface of the artificial skin. The process of bubbling and/or releasing $CO_2$ gas through or from the calcifying solution can be repeated until a sufficient thickness of the coating has been reached.

In a preferred embodiment, the artificial skin is designed to accommodate skin glands (sebaceous, apocrine or eccrine glands), hair follicles or cells from which skin glands or hair follicles may develop. The skin glands or hair follicles may be obtained, for example, from a suitable donor, such as a cadaver, preferably having the same blood type. It is preferred, however, that autologous hair follicles are used, which may be obtained in a biopsy from the patient undergoing a skin transplantation. Cells which may be used having the ability to form or develop into hair follicles are, among others, stem cells, hair follicle dermal papilla, fibroblasts, keratinocytes, germinative matrix cells, and melanocytes. It will be understood that the invention also encompasses an artificial skin provided with skin glands, hair follicles or cells which may develop into hair follicles or skin glands.

In accordance with this embodiment, the artificial skin may for instance be provided with orifices in which hair follicles, or cells which may develop into hair follicles, may be located. These orifices may be created by drilling, possibly by laser drilling, or, and this is preferred, by, punching with a, preferably hollow, needle having the desired diameter. It is also possible to form the artificial skin in a mold provided with protuberances having the form of the desired orifices. The amount of orifices per surface unit of the artificial skin will typically depend on the density of the hair growth on the skin of the patient which is to be treated with the artificial skin. In general, there will be between 1 and 50 orifices per square centimeter. It will be clear that it is aimed at to achieve as natural an appearance of the patient's skin after implantation of the present artificial skin as possible. The diameter of the orifices may vary, dependent on whether hair follicles or cells from which hair follicles may develop are to be provided in the artificial skin. Typically, the diameter will lie between 10 $\mu$m and 10 m. The depth of the orifices will, depending on the thickness of the artificial skin, vary within a range of 5 to 2000 $\mu$m, preferably of 5 to 1500 $\mu$m.

An artificial skin designed to accommodate skin glands or hair follicles according to the invention may be provided with a dense top layer, preferably a semi-permeable membrane as mentioned above or an epidermal equivalent provided with keratinocytes, which may be put on top thereof, and can be kept in place by gluing it to the artificial skin using any biocompatible glue. Of course, it is also possible that the dense layer forms an integral part of the artificial skin. In fact, in accordance with this embodiment it is possible that the entire artificial skin is dense or substantially dense.

The dense top layer contributes to the provision of space and configuration for hair growth. Further, it may assist in keeping the hair in place. When the artificial skin is provided with cells which may form or develop into skin glands or hair follicles, it is also possible to apply the dense top layer on top of an artificial skin not containing orifices. In that case, a substance improving cell adhesion as discussed above, such as integrin, CD2, CD48, laminin or fibronectin, may be applied at the orifices in the artificial skin, thus defining the locations for the skin glands or hair follicles to develop. Through the orifices, cells may be seeded onto the artificial skin, which will adhere to the substance improving cell adhesion. The dense top layer may be removed before or after seeding the cells. It is another advantage of the present artificial skin that it has such an optimal degradation profile that it remains intact long enough to keep a hair, a hair follicle or a skin gland in place, while on the other hand it degrades fast enough to meet all requirements of a tissue engineered artificial skin. In addition, in case the hair follicle, the skin gland or the cells which may develop into a hair follicle or a skin gland is applied to the artificial skin when said skin is in a dry, non-swollen state, the swelling behavior of the artificial skin when in contact with an aqueous environment will greatly contribute to the keeping the hair follicle or skin gland in place.

An orifice in the artificial skin forms a chamber in which the skin gland or hair follicle may be located. Through the orifice in the dense top layer (the semi-permeable membrane), a hair may grow. Also, the dense top layer may assist in keeping the hair in place. It is one of the advantages of the artificial skin according to the invention, that nutrients will be able to reach the skin gland or hair follicle by diffusion. Alternatively, the diffusion may be amplified by providing a channel below the chamber, which is smaller in diameter than the chamber itself, and through which nutrient and waste product transport may take place.

In another preferred embodiment, the artificial skin is provided with biologically active agents, which may be released after implantation of the artificial skin in a patient. Preferred biologically active agents to be incorporated into the artificial skin are vitamins, such as vitamin C or E, antibiotics, such as gentamycin, and growth factors, such as FGF, EGF, TGF-$\alpha$, and IGF-1. The provision of the artificial skin with biologically active agents may be accomplished as described in EP-A-0 830 859, which is incorporated herein by reference.

Above it has been mentioned, that an artificial skin according to the invention can be applied to a wound with or without cells seeded thereon. If a cell-seeded approach is taken, the cells used will preferably be autologous epithelial cells, fibroblasts, or cells that can develop into epithelial cells or fibroblasts. Whether cells are seeded before application or whether a cell-free approach is taken, in accordance with the invention it has been found feasible to apply keratinocytes onto the artificial skin. The provision of the keratinocytes onto the skin may advantageously be carried out in one of three different manners.

In accordance with a first manner, a differentiated (stratified) keratinocyte sheet may be obtained by applying keratinocytes onto a suitable carrier which allows keratinocyte attachment (e.g. of the above described copolymer of a polyalkylene glycol and an aromatic ester) having pores which allow for nutrient and waste material transport. The pores are preferably smaller than 1 $\mu$m. The keratinocytes on the carrier are preferably first cultivated submerged in a suitable culture medium, followed by cultivation at the air-liquid interphase until stratification occurs. Subsequently, the keratinocyte sheet may be detached from the carrier, e.g. using by a protease such as dispase. The thus obtained keratinocyte sheet is preferably applied to an artificial skin according to the invention with its basal side facing the artificial skin. This may be carried out either in vitro or in vivo, wherein in the latter case the artificial skin is applied onto a skin wound.

In accordance with a second manner, keratinocytes are seeded on a dense polymer film which has been provided with holes or pores for nutrient and waste material transport. The film preferably has a thickness of 5–100 $\mu$m, more preferably of 10–80$\mu$m, and is preferably of the above described copolymer of a polyalkylene glycol and an aromatic ester, more preferably of a copolymer of polyethylene glycol and polybutylene terephthalate. The holes or pores preferably have a diameter of less than 1 $\mu$m to prevent migration of keratinocytes across the polymer film. Preferably, the holes or pores are provided in the dense film by laser drilling.

Onto this polymer film, keratinocytes may be seeded to reach a subconfluent or confluent state, at the side which, after application on an artificial skin according to the invention, faces away from the wound. Thus, the polymer film will be provided between the keratinocytes and the artificial skin. Nutrient supply to the keratinocytes may be ensured either via diffusion through the polymer film or through the holes or pores.

In accordance with a third manner, the polymer film as described in the discussion of the second manner is seeded with keratinocytes at its side which is to face an artificial skin according to the invention to which it may be applied. Thus, the keratinocytes are provided between the polymer film and the artificial skin. In one embodiment, the polymer film may be removed soon, preferably within 24 hours, after the film with the keratinocytes has been applied to the artificial skin. The keratinocytes will remain behind, attached to the artificial skin. In another embodiment, the keratinocytes are allowed to form a differentiated cornified epidermis, which leads to a detachment of the (differentiated) keratinocytes from the polymer film, which may then conveniently be removed. The formation of the cornified epidermis will usually take place after the artificial skin with keratinocytes has been applied to a wound. It is preferred that accumulating wound fluid is soaked up by an absorbent material (a dressing) which is placed on the polymer film.

The invention will now be elucidated by the following, non-restrictive example.

EXAMPLE

Materials and Methods

Manufacture and Composition of Polyactive™ Substrate

The material used was an elastomeric Poly(Ethylene Glycol Terephthalate) and Poly(Butylene Terephthalate) (PEGT/PBT) copolymer with a PEGT/PBT ratio of 55/45 and PEG weight average molecular weight ($M_w$) of 300 Dalton [HC Implants BV., Leiden, The Netherlands]. In the literature, this type of polymer is often referred to as PEO/PBT or PEG/PBT copolymer.

The material was subjected to a solvent casting procedure, wherein a substrate was formed by liquefying the material in chloroform containing sodium citrate particles having a particle size of 75–212 µm, to acquire the desired pore structure. The salt/copolymer solution was then casted on a glass plate using a substrate-casting apparatus fixed at a height of approximately 250 µm. The salt particles were allowed to sink, and a substrate was formed wherein the pores gradually changed from one surface to the opposite one (BISKIN-M).

A second substrate was casted analogous to the manner described above. This second substrate was provided with a dense top layer, which was prepared by casting a layer as described above, except that no salt particles were used. This dense top layer was applied on top of the second substrate to obtain the substrate BISKIN.

Standard techniques were used to remove the salt from all substrates (Beumer et al., Clin. Mater., 1993, Vol. 14, pp. 21–26).

Fibroblast Isolation and (Sub)Culture

A split-thickness skin obtained from the rump of a Yucatan miniature pig using a mechanical dermatome was used for establishment of fibroblast culture. The skin biopsies were first extensively washed in phosphate buffered saline (PBS) supplemented with Penicillin (1,000 IU/ml) and Streptomycin (1,000 µg/ml) [ICN Biomedicals, Inc.], subsequently cut into 0.5 $cm^2$ pieces and finally incubated overnight at 4° C. in trypsin solution (0.3% trypsin, 0.15 M NaCl, 0.04% KCl, 0.1% glucose, pH 7.6). Thereafter, the skin specimens were incubated for 60 min at 37° C. after which epidermal cells were mechanically separated from the dermis by means of a forceps. Next, the dermis was digested with a collagenase solution (0.35% collagenase type 1A [Sigma] in a Dulbecco's Modification of Eagle's Essential Medium (DMEM [ICN Biomedicals, Inc], pH 7.6) for 60 min at 37° C. Released fibroblasts were grown in DMEM that was supplemented with 5% Fetal Calf Serum (FCS [Gibco]) and Penicillin (500 U/ml)/Streptomycin (500 µg/ml) [ICN Biomedicals, Inc.]. The medium was refreshed three times a week.

This method usually rendered confluent cultures of fibroblasts within one week, which then were trypsinized (0.5% trypsin in PBS, supplemented with 0.05% EDTA and 0.1% glucose, pH 7.6) and subcultured. Passages one to five were used for the experiments.

Fibroblast Culture on Polyactive™ [300PEG55PBT45]

Gamma irradiated sterile Polyactive™ substrates (BISKIN and BISKIN-M, size 5×5 and 6×6 cm) were immersed in complete culture medium and incubated overnight at 37° C. on polycarbonate filters (0.4 µm [Costar]). Thereafter, the substrates were kept immersed by gluing them on the filter with Histoacryl™ [Melsungen, Germany].

1.5 ml of suspension autologous or allogeneic dermal fibroblasts (200,000–300,000 cells/$cm^2$) were seeded onto the porous layer of the substrates. Cells were allowed to attach for 5 hours after which 14 ml of culture medium were added. The fibroblasts were cultured for three weeks in culture medium supplemented with Epidermal Growth Factor (EGF, 5.0 ng/ml [Sigma]) and ascorbic acid (100 µg/ml [Sigma]). The medium was changed every other day.

Prior to transplantation, the cell-free or fibroblast-populated substrates were washed three times in serum-free medium and directly transported to the operating theatre.

Animal Operation/Transplantation

This study was approved by the Animal Use Committee from the University of Leiden. Five Yucatan miniature pigs weighing 17–23 kg were used. The animals were fed a basal swine diet and housed in animal facilities with controlled temperature (19–21° C.) and light (12 h light/12 h darkness). Immediately prior to the operation the pigs were sedated with a mixture of Stressnil injected intramuscularly, and general anaesthesia was maintained with mask inhalation of isoflurane, oxygen, and nitrous oxide. The backs were shaved, cleansed with chlorhexidine, and covered with Ophraflex™. A maximum of five square wounds (5×5 cm) were marked on the Ophraflex™ on each flank of the animal and subsequently full-thickness slices of skin, subcutaneous fat and panniculus carnosus were excised, exposing the muscle fascia of the external intercostal muscles. Cell-free or cell-seeded substrates (seeded with allogeneic or autologous fibroblasts) were placed into the wounds (Table 1). All wounds were covered with a non-adherent polyamide mesh [Surfasoft, Mediprof, The Netherlands]; fixed with skin staplers [Johnson & Johnson Medical, The Netherlands] or with paraffin impregnated gauzes [Unitulle, Roussel B.V.; The Netherlands]. Finally, the wounds were protected against mechanical trauma by gauze layers, and fixed with adhesive tape [Fixomull™ stretch, Beiersdorf, Hamburg] and elastic stockings [Tubigrip™, Seton Healthcare Group plc., England]. For control, wounds were treated with the bandage as described above, without a dermal substrate.

TABLE 1

All experimental wounds with positions and transplanted substrates as described in Materials and Methods.

| Wound position | Experiment 1 | | Experiment 2 | | |
|---|---|---|---|---|---|
| | pig 1 | pig 2 | pig 3 | pig 4 | pig 5 |
| Left flank | | | | | |
| 1 | A | D | E | F | D |
| 2 | B | E | F | D | E |
| 3 | C | F | D | E | F |
| 4 | D | G | E | F | G |
| 5 | E | A | D | G | F |
| Right flank | | | | | |
| 6 | F | B | F | D | E |
| 7 | G | C | D | E | G |
| 8 | A | D | E | F | D |
| 9 | B | E | F | D | E |
| 10 | C | F | G | E | F |

Macroscopical Transplant Examination

Wounds were inspected, measured and photographed twice a week. The extent of wound contraction was established using a sterile marking gauge and calculating the decrease in surface area of the wound until re-epithelialization occurred. Wound contraction is defined as $$\text{Wound contraction} = \frac{A_0 - A_x}{A_0} * 100\%$$

wherein $A_0$ is the wound area on day zero and $A_x$ is the area on day x post-transplantation. For statistical analysis the Student-t test was used.

Biopsies (5 mm in diameter) were collected under general anesthesia after 17 days and 1, 2, 3, 6, 12 and 24 months post-transplantation. Biopsies were taken from each individual wound. Per wound a maximum of four biopsies were taken. Biopsies were taken from different sites of the wounds.

If, however, in the postoperative period, wrinkles developed in the material, the ridge of the wrinkle was debrided in the operating-room in order to drain the fluid. The dermal substrate was never removed prematurely.

Microscopical Examination

Preparation of Samples for Light and Electron Microscopy

Biopsies and ungrafted dermal substrates were rinsed in saline, dissected, and fixed with a mixture of 2% formaldehyde ([Sigma], freshly prepared from paraformaldehyde), and 1.5% glutaraldehyde [Polysciences, Inc.] in 0.2M Cacodylate buffer, pH 7.4, and subsequently dehydrated in a graded ethanol series up to 100%.

For light microscopy (LM), specimens were embedded in glycol-methyl-methacrylate [Merck]. Sections were cut on a Reichert Jung Supercut 2050 at a thickness of 1–2 i m and stained with Toluidine Blue. Polyactive™ was discriminated from the surrounding tissue using polarized light.

For scanning electron microscopy (SEM), the specimens were critical point dried [(Balzers CPD030], gold sputter-coated [Balzers MED010] and examined with a Philips SEM 525M at 15 kV.

For transmission electron microscopy (TEM) and reflection contrast microscopy (RCM), fixed specimens were briefly rinsed in 0.1M phosphate buffer (pH 7.4) and post-fixed for 1 hour in 1.0% $OsO_4$ and 1.5% $K_4Fe(CN)_6$. Finally, the specimens were washed with phosphate buffer for 10 minutes followed by dehydration through increasing concentrations of ethanol, which were subsequently substituted by EPON resin. After embedding in EPON, ultrathin sections (60–100 nm) were stained with uranyl acetate and lead hydroxide and examined at 80 kV in a Philips EM 410 or were stained with Toluidine Blue and examined in an Orthoplan light microscope.

Immunohistochemistry

Biopsies were embedded in OCT compound (Tissue Tek Miles Inc.), immediately frozen in liquid nitrogen, and stored at −80° C. until use. Five-micrometer thick cryostat sections were cut at −25° C., air-dried overnight, fixed in acetone for 10 minutes, and immunolabelled at room temperature. Multiple sections of each specimen were processed to assure representative samples. The monoclonal antibodies used for this study were directed against: type IV collagen (Dakopatts, Glostrup, Denmark; 1:200), vimentin and smooth muscle actin (Dakopatts, Glostrup, Denmark; 1:200). The sections were incubated with the first antibodies at room temperature for 60 minutes. Thereafter, the sections were washed and further incubated respectively with biotinylated second antibody [Dakopatts, Glostrup, Denmark] for 30 minutes at room temperature, followed by incubation with streptavidin-biotinylated-horseradish-peroxidase complex [Amersham; 1:100] at room temperature for 30 minutes. The sections were soaked in a solution containing 0.005% of 3-amino-9-ethyl carbazole, 0.03% of $H_2O_2$ and sodium acetate buffer, pH 5.0, for 1 to 5 minutes and counter-stained with Mayer's Hematoxylin. As a control, parallel sections incubated with normal serum were used.

Results

Transplantation Material

It was observed using SEM, that all pores of the porous substrate BISKIN-M were filled with fibroblasts and extracellular matrix.

Macroscopical and Microscopical Evaluation Post-transplantation

The general clinical observations concerning healing were the lack of inflammation, contracture or rejection with maintenance of elasticity and suppleness in the healed wound. These observations were made at the various stages of healing, from week one to twenty-four months.

I. Early Post-transplantation Period (Until One Month Post-transplantation)

Adhesion to the Wound

After placement of the BISKIN grafts on the animal wounds it was observed that all BISKIN-substrates showed little or no adherence to the wound bed. Pre-swelling and transplantation site were not of influence to adherence. In contrast to this, the adherence of the BISKIN-M substrates to the underlying wound was, however, achieved within a few minutes after application. Therefore, in further evaluations BISKIN-M Polyactive™ substrates are presented only.

There was no difference between wounds transplanted with cell-free or cell-seeded BISKIN-M substrates in the incidence and the appearance of wrinkles. There were no deaths, wound infections, or acute graft failures in any of the animals.

Vascularization

Four days after grafting of cell-free or cell-seeded BISKIN-M substrates, the grafted area showed red appearance due to the ingrowth of capillary rich granulation tissue. Light and electron microscopy revealed the presence of a thick layer of highly vascularized granulation tissue surrounding the dermal grafts in all experimental wounds. Cells from granulation tissue (mainly fibroblasts, lymphocytes and macrophages) and capillary vessels were invading the pores of the BISKIN-M substrates. There was no difference between cell-free or cell-seeded BISKIN-M dermal grafts, and the density of blood vessels in the subdermal granulation tissue of BISKIN-M treated wounds was markedly higher than in control wounds.

Wound Contraction

All wounds contracted, which was defined as the movement of the wound edges towards the centre of the wound. There were considerable differences, however, in the extent of contraction during the post-transplantation time between substrates tested. The extent of wound contraction was significantly lower in the BISKIN-M-treated wounds as compared to non-treated wounds (controls) ($p<0.05$). In control wounds (without so strate), 50% wound contraction was observed within 14 days post-grafting, whereas wounds treated with the BISKIN-M substrates showed reduction of surface area with 5–15%. 30 days after transplantation a reduction of surface area with cell-seeded and cell-free BISKIN-M substrates treated wounds of 15–40% was observed, whereas control wounds showed 75% reduction. Wounds treated with the autologous-fibroblasts seeded BISKIN-M substrates contracted to a lesser extent as compared to wounds treated with allogeneic-fibroblasts seeded or with cell-free BISKIN-M substrates. These differences, although undoubtedly present, were not statistically significant. ($p<0.15$ when compared to allogeneic-fibroblasts populated BISKIN-M substrates, and $p<0.11$ when compared to cell-free BISKIN-M substrates).

Formation of Granulation Tissue

In the first 2 weeks, macrophage phagocytic activity was observed at most implantation sites. The level of this activity was generally related to the degree of local trauma created by the surgical procedure because it was seen in both control and transplant-treated wounds. After two weeks lymphocytes were present within and around the copolymer transplants. The presence of condensed chromatin in the nucleus of these cells suggests that they were not activated. Cellular debris but also some copolymer fragments were incorporated in macrophages or multinucleated giant cells.

Early Formation of Neo-dermis

In the first week post-operation all wounds were characterised by the presence of a relatively high number of myofibroblasts containing a-smooth muscle actin.

Degradation

Light and transmission electron microscopy showed a foreign body reaction at the implantation site of all transplanted substrates. Macrophages and multinucleated giant cells were present during the first 4 weeks post-transplantation. At 8 weeks post-transplantation the foreign body reaction was ceased. Four weeks after transplantation, matrix degradation was observed. Degradation started with fragmentation of the polymers into particles that were phagocytized by macrophages and multinucleated giant cells.

II. Late Post-transplantation Period (from 2 Up to 24 Months Post-transplantation)

Formation of Neo-dermis

It was observed that, two months after grafting, newly formed collagen in wounds treated with fibroblast-populated Polyactive substrates, was distributed in orthogonal arrays, or in a "basket wave" pattern. The organisation of collagen bundles and blood vessel formation was similar in wounds transplanted with substrates seeded with allogeneic- or autologous-fibroblasts.

Degradation

Twenty-four months post-transplantation, the tissue surrounding the Polyactive substrates consisted of a mature connective tissue. At the macroscopic and at the light- and electron microscopic level, the heart, spleen, liver, lung, glands and kidneys did not show any signs of swelling, tissue damage/necrosis or polymer fragments. The most important results on the appearance of wounds after grafting are summarised in Table 2.

TABLE 2

Characteristics of wounds transplanted with cell-free or fibroblast-populated BISKIN-M matrices.

| | | treatment of the wounds | | |
|---|---|---|---|---|
| Parameters | | none | cell-free Polyactive | fibroblast-populated Polyactive* |
| adhesion | time after application | | 1–2 min | 1–2 min |
| vascularization | time after application | >14 days | in 4 days | in 4 days |
| wound contraction | 30 days after application | >50% | <50% | <50% |
| neo-dermis formation | collagen appearance | thin, less compact bundles | thin, less compact bundles | thick, compact bundles |
| | collagen distribution | in parallel arrays | in parallel arrays | in orthogonal arrays |
| degradation | number of intracellularly located fragments | | high | low | seeded with autologous or allogeneic fibroblasts

What is claimed is:

1. Artificial skin comprising a copolymer of a polyalkylene glycol and an aromatic polyester, said artificial skin comprised of a single layer having a thickness between 50 and 2000 μm and having an upper and a lower side comprising pores with the upper and the lower side each having a macroporosity between 10% and 95%.

2. Artificial skin according to claim 1 wherein the upper and the lower side each has a macroporosity of at least 15%.

3. Artificial skin according to claim 1 wherein the upper and the lower side each has a macroporosity of at least 20%.

4. Artificial skin according to claim 1 comprising pores having a diameter between 20 and 500 μm.

5. Artificial skin according to claim 1 comprising pores having a diameter between 50 and 250 μm.

6. Artificial skin according to claim 1 wherein the aromatic polyester comprises an alkylene glycol having from 2 to 8 carbon atoms and an aromatic dicarboxylic acid.

7. Artificial skin according to claim 1 wherein the polyalkylene glycol comprises one or more of polyethylene glycol, polypropylene glycol, or polybutylene glycol.

8. Artificial skin according to claim 1 wherein the aromatic polyester is one or more of poly(ethyleneterephthalate), poly(propyleneterephthalate), and poly(butyleneterephthalate).

9. Artificial skin according to claim 1 wherein the copolymer is a polyethylene glycol/poly(butyleneterephthalate) copolymer.

10. Artificial skin according to claim 1 wherein the copolymer comprises 40–80 wt. % of the polyalkylene glycol.

11. Artificial skin according to claim 1 wherein the copolymer comprises 50–70 wt. % of the polyalkylene glycol.

12. A method of using artificial skin according to claim 1 comprising contacting the artificial skin to a wound of an animal or human.

13. A method according to claim 12 wherein the artificial skin comprises autologous epithelial cells and/or autologous fibroblasts.

14. Artificial skin comprising a copolymer of a polyalkylene glycol and an aromatic polyester, said artificial skin having a thickness between 50 and 2000 µm and having an upper and a lower side comprising pores with the upper and the lower side each having a macroporosity between 10% and 95%, wherein the pores at the upper side have a diameter smaller than the diameter of the pores at the lower side.

15. Artificial skin according to claim 14 wherein the pores at the upper side have a diameter of between 0.2 and 5 µm.

16. Artificial skin according to claim 14 wherein the pores at the lower side have a diameter of between 20 and 500 µm.

17. Artificial skin according to claim 14 wherein the aromatic polyester comprises an alkylene glycol having from 2 to 8 carbon atoms and an aromatic dicarboxylic acid.

18. Artificial skin according to claim 14 wherein the polyalkylene glycol comprises one or more of polyethylene glycol, polypropylene glycol, or polybutylene glycol.

19. Artificial skin according to claim 14 wherein the aromatic polyester is one or more of poly(ethyleneterephthalate), poly(propyleneterephthalate), and poly(butyleneterephthalate).

20. Artificial skin according to claim 14 wherein the copolymer is a polyethylene glycol/poly(butyleneterephthalate) copolymer.

21. Artificial skin according to claim 14 wherein the copolymer comprises 40–80 wt. % of the polyalkylene glycol.

22. Artificial skin according to claim 14 wherein the copolymer comprises 50–70 wt. % of the polyalkylene glycol.

23. A method of using artificial skin according to claim 14 comprising contacting the artificial skin to a wound of an animal or human.

24. Artificial skin comprising a copolymer of a polyalkylene glycol and an aromatic polyester, said artificial skin having a thickness between 50 and 2000 µm and having an upper and a lower side comprising pores with the upper and the lower side each having a macroporosity between 10% and 95%, and the artificial skin comprising autologous cells.

25. Artificial skin according to claim 24 wherein the autologous cells comprise epithelial cells or fibroblasts.

26. Artificial skin according to claim 24 wherein the aromatic polyester comprises an alkylene glycol having from 2 to 8 carbon atoms and an aromatic dicarboxylic acid.

27. Artificial skin according to claim 24 wherein the polyalkylene glycol comprises one or more of polyethylene glycol, polypropylene glycol, or polybutylene glycol.

28. Artificial skin according to claim 24 wherein the aromatic polyester is one or more of poly(ethyleneterephthalate), poly(propyleneterephthalate), and poly(butyleneterephthalate).

29. Artificial skin according to claim 24 wherein the copolymer is a polyethylene glycol/poly(butyleneterephthalate) copolymer.

30. Artificial skin according to claim 24 wherein the copolymer comprises 40–80 wt. % of the polyalkylene glycol.

31. Artificial skin according to claim 24 wherein the copolymer comprises 50–70 wt. % of the polyalkylene glycol.

32. A method of using artificial skin according to claim 24 comprising contacting the artificial skin to a wound of an animal or human.

33. Artificial skin comprising a copolymer of a polyalkylene glycol and an aromatic polyester, said artificial skin having a thickness between 50 and 2000 µm and having an upper and a lower side comprising pores with the upper and the lower side each having a macroporosity between 10% and 95%, and the artificial skin comprising a calcium phosphate coating.

34. Artificial skin according to claim 33 wherein the aromatic polyester comprises an alkylene glycol having from 2 to 8 carbon atoms and an aromatic dicarboxylic acid.

35. Artificial skin according to claim 33 wherein the polyalkylene glycol comprises one or more of polyethylene glycol, polypropylene glycol, or polybutylene glycol.

36. Artificial skin according to claim 33 wherein the aromatic polyester is one or more of poly(ethyleneterephthalate), polypropyleneterephthalate), and poly(butyleneterephthalate).

37. Artificial skin according to claim 33 wherein the copolymer is a polyethylene glycol/poly(butyleneterephthalate) copolymer.

38. Artificial skin according to claim 33 wherein the copolymer comprises 40–80 wt. % of the polyalkylene glycol.

39. Artificial skin according to claim 33 wherein the copolymer comprises 50–70 wt. % of the polyalkylene glycol.

40. A method of using artificial skin according to claim 33 comprising contacting the artificial skin to a wound of an animal or human.

41. Artificial skin comprising a copolymer of a polyalkylene glycol and an aromatic polyester, said artificial skin having a thickness between 50 and 2000 µm and having an upper and a lower side comprising pores with the upper and the lower side each having a macroporosity between 10% and 95%, and the artificial skin designed to accommodate skin glands, hair follicles or cells from which skin glands or hair follicles may develop.

42. Artificial skin according to claim 41 wherein the aromatic polyester comprises an alkylene glycol having from 2 to 8 carbon atoms and an aromatic dicarboxylic acid.

43. Artificial skin according to claim 41 wherein the polyalkylene glycol comprises one or more of polyethylene glycol, polypropylene glycol, or polybutylene glycol.

44. Artificial skin according to claim 41 wherein the aromatic polyester is one or more of poly(ethyleneterephthalate), poly(propyleneterephthalate), and poly(butyleneterephthalate).

45. Artificial skin according to claim 41 wherein the copolymer is a polyethylene glycol/poly(butyleneterephthalate) copolymer.

46. Artificial skin according to claim 41 wherein the copolymer comprises 40–80 wt. % of the polyalkylene glycol.

47. Artificial skin according to claim 41 wherein the copolymer comprises 50–70 wt. % of the polyalkylene glycol.

48. A method of using artificial skin according to claim 41 comprising contacting the artificial skin to a wound of an animal or human.

49. Artificial skin comprising a copolymer of a polyalkylene glycol and an aromatic polyester, said artificial skin having a thickness between 50 and 2000 µm and having an upper and a lower side comprising pores with the upper and the lower side each having a macroporosity between 10% and 95%, and the artificial skin comprising skin glands, hair follicles or cells which may develop into skin glands or hair follicles.

50. Artificial skin according to claim 49 wherein the aromatic polyester comprises an alkylene glycol having from 2 to 8 carbon atoms and an aromatic dicarboxylic acid.

51. Artificial skin according to claim 49 wherein the polyalkylene glycol comprises one or more of polyethylene glycol, polypropylene glycol, or polybutylene glycol.

52. Artificial skin according to claim 49 wherein the aromatic polyester is one or more of poly(ethyleneterephthalate), poly(propyleneterephthalate), and poly(butyleneterephthalate).

53. Artificial skin according to claim 49 wherein the copolymer is a polyethylene glycol/poly(butyleneterephthalate) copolymer.

54. Artificial skin according to claim 49 wherein the copolymer comprises 40–80 wt. % of the polyalkylene glycol.

55. Artificial skin according to claim 49 wherein the copolymer comprises 50–70 wt. % of the polyalkylene glycol.

56. A method of using artificial skin according to claim 49 comprising contacting the artificial skin to a wound of an animal or human.

57. Artificial skin comprising a copolymer of a polyalkylene glycol and an aromatic polyester, said artificial skin having a thickness between 50 and 2000 μm and having an upper and a lower side comprising pores with the upper and the lower side each having a macroporosity between 10% and 95%, and the artificial skin comprising a biologically active agent.

58. Artificial skin according to claim 57 wherein the aromatic polyester comprises an alkylene glycol having from 2 to 8 carbon atoms and an aromatic dicarboxylic acid.

59. Artificial skin according to claim 57 wherein the polyalkylene glycol comprises one or more of polyethylene glycol, polypropylene glycol, or polybutylene glycol.

60. Artificial skin according to claim 57 wherein the aromatic polyester is one or more of poly(ethyleneterephthalate), poly(propyleneterephthalate), and poly(butyleneterephthalate).

61. Artificial skin according to claim 57 wherein the copolymer is a polyethylene glycol/poly(butyleneterephthalate) copolymer.

62. Artificial skin according to claim 57 wherein the copolymer comprises 40–80 wt. % of the polyalkylene glycol.

63. Artificial skin according to claim 57 wherein the copolymer comprises 50–70 wt. % of the polyalkylene glycol.

64. A method of using artificial skin according to claim 57 comprising contacting the artificial skin to a wound of an animal or human.

65. Artificial skin comprising a copolymer of a polyalkylene glycol and an aromatic polyester, said artificial skin having a thickness between 50 and 2000 μm and having an upper and a lower side comprising pores with the upper and the lower side each having a macroporosity between 10% and 95%, and the artificial skin comprising keratinocytes.

66. Artificial skin according to claim 65 wherein the aromatic polyester comprises an alkylene glycol having from 2 to 8 carbon atoms and an aromatic dicarboxylic acid.

67. Artificial skin according to claim 65 wherein the polyalkylene glycol comprises one or more of polyethylene glycol, polypropylene glycol, or polybutylene glycol.

68. Artificial skin according to claim 65 wherein the aromatic polyester is one or more of poly(ethyleneterephthalate), poly(propyleneterephthalate), and poly(butyleneterephthalate).

69. Artificial skin according to claim 65 wherein the copolymer is a polyethylene glycol/poly(butyleneterephthalate) copolymer.

70. Artificial skin according to claim 65 wherein the copolymer comprises 40–80 wt. % of the polyalkylene glycol.

71. Artificial skin according to claim 65 wherein the copolymer comprises 50–70 wt. % of the polyalkylene glycol.

72. A method of using artificial skin according to claim 65 comprising contacting the artificial skin to a wound of an animal or human.

* * * * *